United States Patent [19]

Balasubramanyan et al.

[11] 4,086,351
[45] Apr. 25, 1978

[54] 1,2,4-TRIAZOLE-CONTAINING COMPOUNDS AND THEIR USE AS PESTICIDES

[75] Inventors: Sugavanam Balasubramanyan, Wokingham; Margaret Claire Shephard, Maidenhead, both of England

[73] Assignee: Imperial Chemical Industries Limited, London, England

[21] Appl. No.: 729,864

[22] Filed: Oct. 5, 1976

[30] Foreign Application Priority Data

Oct. 9, 1975   United Kingdom ............... 41449/75
Aug. 20, 1976  United Kingdom ............... 34836/76

[51] Int. Cl.² .................. A01N 9/00; A61K 31/41; C09B 23/00
[52] U.S. Cl. .................. 424/269; 260/308 R; 424/273 R; 542/405; 542/429; 542/431
[58] Field of Search ............... 260/240 J, 308 R; 424/269, 273

[56] References Cited
U.S. PATENT DOCUMENTS

| | | | |
|---|---|---|---|
| 3,503,952 | 3/1970 | Caldwell et al. | 260/240 J X |
| 3,721,668 | 3/1973 | Rufer et al. | 260/240 J |
| 3,978,069 | 8/1976 | Büchel et al. | 260/309 X |

*Primary Examiner*—Robert V. Hines
*Attorney, Agent, or Firm*—Cushman, Darby & Cushman

[57] ABSTRACT

Plant fungicidal compounds of formula:

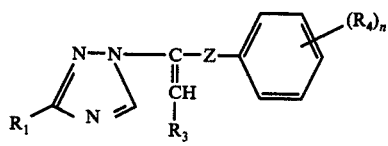

wherein $R_1$ is hydrogen, or nitro, $R_3$ is alkyl, furyl, thienyl or phenyl, $R_4$ is hydrogen, halogen, nitro, phenyl, alkoxy or alkyl, $n$ is 1, 2 or 3, and Z is C=O or a derivative thereof; and their salts.

11 Claims, No Drawings

1,2,4-TRIAZOLE-CONTAINING COMPOUNDS AND THEIR USE AS PESTICIDES

This invention relates to heterocyclic compounds which are imidazole or 1,2,4-triazole compounds, to a process for preparing them, to compositions containing them and to a method of combating fungal pests using them.

The compounds have the general formula (I):

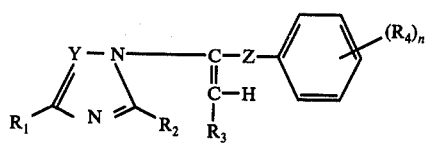

wherein Y is =N— or =C(R)—, each of R, $R_1$ and $R_2$, which may be the same or different, is hydrogen, halogen, nitro or alkyl (e.g. methyl, ethyl, propyl or butyl); $R_3$ is hydrogen or furyl, thienyl or hydrocarbyl optionally substituted with halogen, acyloxy, cyano, hydroxy, nitro, alkoxy or unsubstituted or halo-substituted alkyl; $R_4$ is hydrogen, halogen, nitro, phenyl, alkoxy or unsubstituted or halo-substituted alkyl; n is an integer of 1 to 5; and Z is C=O or a derivative thereof (e.g. an imine, oxime, ketal, hydrazone or semicarbazone), or salts of said compounds.

The compounds form geometrical isomers. The invention includes within its scope such isomers each of which can be isolated from mixtures thereof by methods known in the art.

The term "hydrocarbyl" as used herein refers to monovalent organic radicals composed of hydrogen and carbon. The hydrocarbyl may be saturated or unsaturated, straight or branched chain or single ring; examples are alkyl, alkenyl, alkynyl, cycloalkyl, aryl, aralkyl and alkaryl.

The hydrocarbyl is preferably $C_{1-7}$, especially $C_{1-6}$, hydrocarbyl, e.g. methyl, ethyl, propyl (n- or iso-propyl), butyl (n-, iso- or t-butyl), amyl, hexyl, heptyl, allyl, propynyl, phenyl, benzyl and substituted phenyl and benzyl. The alkoxy is suitably $C_{1-7}$ alkoxy, e.g. methoxy, ethoxy, propoxy or butoxy.

The halogen can be fluorine, chlorine, bromine or iodine. A suitably acyloxy group is acetoxy.

As indicated above, $R_3$ can be substituted phenyl. Specific examples of such groups are 2-chloro- or fluorophenyl, 3-fluorophenyl, 4-fluoro-, chloro-, nitro-, n-butoxy-, methoxy-, cyano-, hydroxy- or acetoxy-phenyl, 2,4-, 3,4- or 2,6-dichlorophenyl, 2,4-dimethoxyphenyl or biphenyl.

Another suitable $R_3$ group is trichloromethyl.

When $R_3$ is thienyl or furyl, it is preferably 2-thienyl, 2-furyl or 5-chloro-2-thienyl.

When n is 1, $R_4$ is preferably fluorine, chlorine or phenyl. When n is 2, the two $R_4$ groups are preferably halogen, e.g. two chlorine atoms in 2- and 4-positions. A suitable halo-substituted alkyl is trifluoro- or trichloromethyl.

The salts can be salts with inorganic or organic acids, e.g. hydrochloric, nitric, sulphuric, acetic or oxalic acid.

Examples of suitable triazole and imidazole compounds are given in, respectively, Tables I and II, wherein Z is C=O.

TABLE I

| Compound No | $R_1$ | $R_2$ | $R_3$ | $R_4$ | Melting (Or Boiling) Point ° C |
|---|---|---|---|---|---|
| 1 | H | H | n-$C_3H_7$ | 4-Cl | (165° /0.5 mm Hg) |
| 2 | H | H | $C_6H_5$ | 4-Cl | 115–117° |
| 3 | H | H | 4-Cl—$C_6H_4$ | 4-Cl | 186–188° |
| 4 | H | H | $C_6H_5$ | H | 125–127° |
| 5 | H | H | 4-$NO_2$—$C_6H_4$ | 4-Cl | 161–163° |
| 6 | H | H | 4-MeO—$C_6H_4$ | 4-Cl | 79–82° |
| 7 | H | H | 4-Cl—$C_6H_4$ | H | 115–116° |
| 8 | H | H | 4-CN—$C_6H_4$ | H | 128–132° |
| 9 | H | H | 2-thienyl | 4-Cl | 113–114° |
| 10 | H | H | 2-furyl | H | 112–114° |
| 11 | H | H | 2,4-di-Cl—$C_6H_3$ | 4-Cl | 98–101° |
| 12 | H | H | 4-F-$C_6H_4$ | 4-Cl | 167–169° |
| 13 | H | H | 2,4-di-MeO—$C_6H_3$ | 4-Cl | 127–129° |

TABLE II

| Compound No | R, $R_1$ and $R_2$ | $R_3$ | $R_4$ | M.P. (° C) |
|---|---|---|---|---|
| 28 | H | 4-Cl—$C_6H_4$ | 4-Cl | 120–122° |
| 29 | H | 4-Cl—$C_6H_4$ | 2,4-di-Cl | 46–48° |
| 30 | H | 2,6-di-Cl—$C_6H_3$ | 4-F | 115–117° |
| 31 | H | 2,6-di-Cl—$C_6H_3$ | 4-F | 95–97° |
| 32 | H | 4-Cl—$C_6H_4$ | 4-F | 143–145° |
| 33 | H | 4-$NO_2$—$C_6H_4$ | 4-F | 55–58° |
| 34 | H | 2,4-di-Cl—$C_6H_3$ | 4-Cl | 130–132° |
| 35 | H | 2,4-di-Cl—$C_6H_3$ | H | 120–122° |
| 36 | H | 4-$NO_2$—$C_6H_4$ | H | 154–156° |
| 37 | H | 4-Cl—$C_6H_4$ | H | 85–87° |
| 38 | H | 2-Cl—$C_6H_4$ | 4-Cl | 147–149° |
| 39 | H | 4-$NO_2$—$C_6H_4$ | 4-Cl | 112–114° |
| 40 | H | 2-Cl—$C_6H_4$ | H | 109–110° |
| 41 | H | 4-$NO_2$—$C_6H_4$ | 4-F | 143–144° |
| 42 | H | 4-$NO_2$—$C_6H_4$ | H | 158–160° |
| 43 | H | 2,6-di-Cl—$C_6H_3$ | H | 117–119° |
| 44 | H | 2-F-$C_6H_4$ | H | 130–132° |
| 45 | H | 2,6-di-Cl—$C_6H_3$ | H | 168–170° |
| 46 | H | 2-F—$C_6H_4$ | 4-Cl | 129–131° |
| 47 | H | $C_6H_5$ | H | 108–110° |
| 48 | H | 3-F—$C_6H_4$ | H | 130–132° |
| 49 | H | 4-F—$C_6H_4$ | H | 85–86° |
| 50 | H | $C_6H_5$ | 4-Cl | 148–150° |
| 51 | H | $C_6H_5$ | 4-F | 133–135° |
| 52 | H | 3-F—$C_6H_4$ | 4-Cl | 131–132° |
| 53 | H | 2-Cl—$C_6H_4$ | 4-F | 105–107° |
| 54 | H | 4-F—$C_6H_4$ | 4-F | 120–121° |
| 55 | H | 2,6-di-Cl—$C_6H_3$ | 4-Cl | 115–116° |
| 56 | H | 2-Cl—$C_6H_4$ | 2,4-di-Cl | 102–104° |
| 57 | H | $C_6H_5$ | 2,4-di-Cl | 76–78° |
| 58 | H | 3,4-di-Cl—$C_6H_3$ | 2,4-di-Cl | 129–131° |
| 59 | H | 2,6-di-Cl—$C_6H_3$ | 2,4-di-Cl | 126–128° |
| 60 | H | 4-F—$C_6H_4$ | 2,4-di-Cl | 86–88° |
| 61 | H | 5-chloro-2-thienyl | H | |
| 62 | H | n-Pr | 4-Cl | |
| 63 | H | 2,4-di-Cl—$C_6H_3$ | 4-Ph | |

It is believed that Compounds 1 to 22, 24 to 40, 43, 44 and 46 to 63 have the configuration (A), and that Compounds 23, 41, 42 and 45 are geometric isomers of Compounds 12, 33, 36 and 43, respectively, and it is believed that they have the configuration (B).

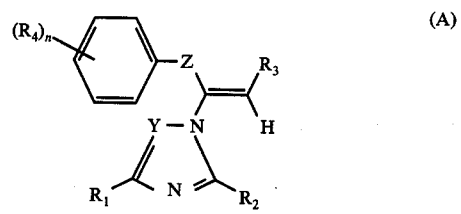

(A)

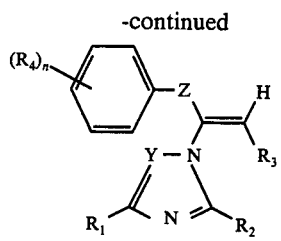

The compounds of general formula (I) may be made by reacting a compound of general (II):

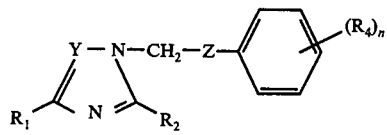

wherein Z, Y, $R_1$, $R_2$, $R_4$ and $n$ are as defined above, or a salt thereof, with an optionally substituted aldehyde, using methods set out in literature.

The reaction is suitably performed in the presence of a convenient base such as piperidine or pyridine in a high boiling hydrocarbon solvent e.g. toluene. Suitably a few drops of glacial acetic acid are present in the reaction mixture as a catalyst.

This process is generally performed by refluxing the reactants together in a solvent and, after allowing reaction to occur, isolating the product by removal of the solvent in vacuo. The product is then crystallised from a convenient solvent. In some cases both geometric isomers are formed in the reaction and these can be conveniently separated by chromatographic techniques. For example, the mixture of isomers can generally be chromatographed on silica as the stationary phase using a mixture of ethyl acetate/petroleum ether as the mobile eluent.

The acetophenone starting material of general formula (II) can be made by reacting an imidazole or triazole with the appropriate α-haloketone (e.g. an α-chloro or bromoketone), using any of the methods set out in the literature. Usually the α-haloketone, in a convenient solvent (preferably acetonitrile or a hydroxylated solvent), is added to the imidazole or triazole in the same solvent at low temperatures. The product can be isolated by removal of the solvent and extracting the residue into an organic solvent with washing. Removal of the solvent gives the required compound which can be crystallised from a convenient solvent.

Alternatively, the compounds of general formula (I) can be made by dehydrogenating in known manner a compound of general formula (III):

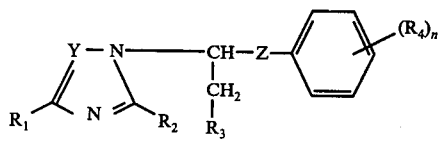

wherein $n$, Y, Z and $R_1$ to $R_4$ are as defined above, or a salt thereof. The dehydrogenation can be achieved for example by reaction with bromine in acetic acid followed by dehydrobromination, or directly by reaction with 2,3-dichloro-5,6-dicyano-1,4-benzoquinone (DDQ).

The compounds wherein Z is a derivative of C=O may be made from the respective carbonyl compound using any of the standard techniques set out in the literature.

The compounds are active against a wide range of fungal diseases, particularly against the following:

*Puccinia recondita* and other rusts on wheat and rusts on other hosts

*Plasmopara viticola* on vines

*Erysiphe graminis* (powdery mildew) on barley and wheat and other powdery mildews on various hosts such as *Sphaerotheca fuliginea* on cucumbers, *Podosphaera leucotricha* on apples and *Uncinula necator* on vines

*Botrytis cinerea* (grey mould) on tomatoes, strawberries, vines, and other hosts

*Piricularia oryzae* on rice

*Colletotrichum lindemuthianum*

*Phytophthora infestans* (late blight) on potato and tomato

Some of the compounds have also shown a broad range of activities against fungi in vitro.

Further some of the compounds are active in the form of seed dressings against Fusarium spp., Septoria spp., Tilletia spp. and Pyrenophora spp. on cereals.

They also have certain plant growth regulating, herbicidal, anti-bacterial, algicidal and anti-viral activities.

The compounds may be used as such for anti-fungal purposes but are more conveniently formulated into compositions.

The invention therefore also provides a fungicidal composition comprising, as an active ingredient, an imidazole or triazole compound or salt thereof as defined above, and a carrier for the active ingredient.

The invention also provides a method for combating fungal diseases in a plant, which method comprises treating the plant, seed of the plant or the locus surrounding the plant or seed with an imidazole or triazole compound or salt thereof as hereinbefore defined.

The compounds can be used to combat plant pests and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foliage, stems, branches or roots, or to soil surrounding the roots.

The term "treating" as used herein refers to all these modes of application and the term "plant" includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen — or phosphorus — containing fertilisers). Compositions comprising only granules of fertiliser incorporating, for example coated with, the triazole compound, are preferred. The invention therefore also provides a fertiliser composition comprising the compound.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents.

Suitable cationic agents are quaternary ammonium compounds for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates). Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10-85%, generally 25-60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity (e.g. growth stimulating substances such as the gibberellins), as well as stabilising agent(s), for example epoxides (e.g. epichlorhydrin).

The following Examples illustrate the invention; the temperatures are given in degrees Centigrade (° C).

EXAMPLE 1

1-(1,2,4-Triazol-1-yl)-p-chlorophenacylstyrene (Compound 2)

Stage I. To α-bromo-p-chloroacetophenone (4.64 g) in acetonitrile (50 ml) was added 1,2,4-triazole (1.4 g) followed by triethylamine (2 g). The mixture was stirred at room temperature for two hours and refluxed for one hour. The solvent was removed under reduced pressure and to the residue water was added. The yellow solid which precipitated was filtered, washed with water and dried. Crystallisation from ethanol-petroleum ether (60°–80°) gave α-1,2,4-triazol-1-yl-p-chloroacetophenone as cream coloured plates, m.p. 148°–150°.

Stage II. α-1,2,4-Triazol-1-yl-p-chloroacetophenone (3.35 g), benzaldehyde (1.59 g) and piperidine (6 drops) in toluene (30 ml) were refluxed in a azeotropic set up until no more water separated; this took about eight hours. The toluene was removed in vacuo and the residue was taken up in methylene chloride. The organic layer was washed with water, dried (MgSO$_4$) and the solvent was removed. The residual oil solidified on cooling. Crystallisation from ethanol-petroleum ether (60°–80°) gave the title compound as a yellow crystalline solid, m.p. 115°–117°.

Compound 2 can also be made by the following procedure. α-Benzyl-α-triazol-1-yl-p-chloroacetophenone (1.6 g) in acetic acid (15 ml) was treated with bromine (0.8 g) and the mixture was refluxed for six hours. The thin layer chromatography over silica gel showed that two components were present in the reaction mixture and there was no change after further refluxing. Acetic acid was then evaporated off in vacuo. The residue was treated with water and was extracted with methylene chloride. The organic layer was washed with water, sodium bicarbonate solution and water and was then dried (Na$_2$SO$_4$). The solvent was removed, and the residual oil was chromatographed over silica gel (60–120 mesh) eluting with petroleum ether (60°–80°) ethyl acetate (1:1) to give, in low yield, the title compound as a pale yellow solid, m.p. 115°–117°.

EXAMPLE 2

1-(1,2,4-Triazol-1-yl)-1-p-chlorophenacyl-p-fluorostyrene (Compounds 12 and 23)

α-1,2,4-Triazol-1-yl-p-chloroacetophenone (25 g), p-fluorobenzaldehyde (14.25 g), piperidine (10 drops) and acetic acid (20 drops) in toluene (200 ml) were refluxed in an azeotropic set up until no more water separated out; this took about two hours. Removal of toluene gave a yellow solid which was crystallised from ethyl acetate/petroleum ether (60°–80°). One of the geometrical isomers of 1-(1,2,4-triazol-1-yl)-1-p-chlorophenyl-p-fluorostyrene was obtained as a yellow crystalline solid, m.p. 167°–169°. The other isomer was isolated from the filtrate by preparative thin layer chromatography on silica gel (Merck silica gel F-254) using ethyl acetate/petroleum ether (60°–80°) (1:1) as the eluent. Crystallisation from ethyl acetate/petroleum ether (60°–80°) gave this isomer, m.p. 114°–115°.

EXAMPLE 3

1-Imidazol-1-yl-1-phenacyl-o-fluorostyrene (Compound 44)

Stage I. Phenacyl bromide (0.05 mol) and imidazole (0.02 mol) were stirred in methanol (50 ml) at 0° for 3 hours. The methanol was removed in vacuo and the residue taken up in methylene chloride (300 ml), washed with water (3 × 100 ml), and dried (anhydrous sodium sulphate). Removal of the solvent left a solid residue which on recrystallisation from ethyl acetate gave 2-(imidazol-1-yl)-acetophenone (60%) as light brown needles, m.p. 112°–113°.

Stage II. 2-(Imidazol-1-yl)-acetophenone (0.03 mol), 2-fluorobenzaldehyde (0.03 mol), piperidine (2 drops), and glacial acetic acid (4 drops), were refluxed in toluene (25 mls) for 10 hours. The solvent was then removed in vacuo and the resultant brown solid washed with ethyl acetate/petroleum ether. Recrystallisation from ethyl acetate gave 1-imidazol-1-yl-1-phenacyl-o-fluorostyrene as pale yellow crystals.

EXAMPLE 4

1-Imidazol-1-yl-1-phenacyl-p-nitrostyrene (Compounds 36 and 42)

2-(Imidazol-1-yl)-acetophenone (0.03 mol), 4-nitro benzaldehyde (0.03 mol), piperidine (2 drops), and glacial acetic acid (4 drops), were refluxed in toluene (50 ml) for 10 hours. The solvent was then removed in vacuo and the resultant brown solid purified by column chromatography on silica eluting with ethyl acetate/petroleum ether (7:3) to give Compound 42 as a pale yellow crystalline solid, m.p. 158°–160° (ethyl acetate/petroleum ether), and Compound 36 as a pale yellow crystalline solid, m.p. 154°–156° (ethyl acetate/petroleum ether).

EXAMPLE 5

The imidazole and triazole compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil and foliage one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:

4 = No disease
3 = 0–5%
2 = 6–25%
1 = 26–60%
0 = >60%

The results are shown in Table III.

TABLE III

| | DISEASE CONTROL | | | | | |
|---|---|---|---|---|---|---|
| Compound No | Puccinia recondita in wheat | Phytophthora infestans in tomato | Plasmopara viticola in vines | Piricularia oryzae in rice | Botrytis cinerea in tomatoes | Erysiphe graminis in barley |
| 1 | 3 | 2 | 3 | 0 | 0 | 4 |
| 2 | 3 | 2–3 | 3 | 3 | 2–4 | 4 |
| 3 | 1–2 | 0 | 2–3 | 0 | 0 | 4 |
| 4 | 3 | 0–1 | — | 0 | — | 4 |
| 5 | 3 | 0 | — | 0–1 | 3 | 4 |
| 6 | 1–2 | 1–2 | — | 0 | 2–3 | 4 |
| 7 | 3 | 0 | — | 0 | 3 | 4 |
| 8 | 3 | 3 | — | 0 | 3 | 4 |
| 9 | 2 | 2 | 0 | 0 | 2 | 4 |
| 10 | 1 | 0 | 0 | 0 | 0 | 4 |
| 11 | 4 | 2 | 2 | 0 | 0 | 4 |
| 12 | 3 | 0 | 1 | 0 | 0 | 3 |
| 13 | 1 | 0 | 1 | — | 1 | 4 |
| 14 | 1 | 3 | 2 | — | 3 | 4 |
| 15 | 1 | 0 | 1 | — | 2 | 4 |
| 16 | 4 | 0 | 3 | 0 | 0 | 0 |
| 17 | 3 | 0 | 3 | 0 | 3 | 4 |
| 18 | 3 | 0 | 0 | — | 0 | 0 |
| 19 | 1 | 0 | 3 | — | 0 | 0 |
| 20 | 3 | 0 | 2 | 0 | 3 | 4 |
| 21 | 4 | — | 3 | 3 | 3 | 4 |
| 22 | 1 | 0 | 0 | 0 | 0 | 2 |
| 23 | 4 | 2 | 3 | 1 | 4 | 4 |
| 24 | 0 | 3 | 3 | — | 2 | 3 |
| 25 | 0 | 3 | 0 | — | 0 | 4 |
| 26 | 3 | 3 | 2 | 4 | 3 | 3 |
| 27 | 3 | 0 | 1 | 0 | 3 | 2 |
| 28 | 3 | 0 | 3 | 0 | 1 | 3 |

TABLE III-continued

| Compound No | Puccinia recondita in wheat | Phytophthora infestans in tomato | Plasmopara viticola in vines | Piricularia oryzae in rice | Botrytis cinerea in tomatoes | Erysiphe graminis in barley |
|---|---|---|---|---|---|---|
| 29 | 3 | 0 | 4 | 0 | 0 | 4 |
| 30 | 3 | 0 | 0 | — | 1 | 1 |
| 31 | 3 | 0 | 3 | — | 0 | — |
| 32 | 3 | 0 | 2 | 0 | 3 | 4 |
| 33 | 3 | 0 | 0 | 2 | 1 | 3 |
| 34 | 3 | 2 | 1 | 0 | 2 | 3 |
| 35 | 3 | 1 | 3 | 0 | 4 | 4 |
| 36 | 3 | 3 | 2 | 1 | 3 | 4 |
| 37 | 3 | 3 | 3 | 0 | 3 | 3 |
| 38 | 0 | 0 | 0 | 0 | 4 | 3 |
| 39 | 3 | 3 | 3 | 1 | 4 | 3 |
| 40 | 3 | 2 | 3 | 0 | 4 | 3 |
| 41 | 3 | 0 | 1 | 2 | 3 | 4 |
| 42 | 3 | 1 | 2 | 0 | 2 | 4 |
| 43 | 0 | — | — | 1 | 3 | 2 |
| 44 | 3 | — | — | 0 | 1 | 3 |
| 45 | 1 | 0 | 0 | 0 | 0 | 2 |
| 46 | 3 | — | — | 0 | 1 | 3 |
| 47 | 3 | — | — | 0 | 3 | 3 |
| 48 | 3 | — | — | 0 | 3 | 3 |
| 49 | 4 | 0 | 0 | 0 | 4 | 3 |
| 50 | 3 | 0 | 0 | 0 | 1 | 2 |
| 51 | 3 | 0 | 0 | 0 | 2 | 3 |
| 52 | 3 | 2 | 1 | 1 | 3 | 3 |
| 53 | 3 | 0 | 0 | 0 | 3 | 3 |
| 54 | 4 | 0 | 0 |   | 3 | 4 |
| 55 |   | 0 | 0 | 3 | 3 | 3 |
| 56 | 3 | 2 | 0 | 0 | 4 | 4 |
| 57 | 3 | 2 | 1 | 0 | 3 | 4 |
| 58 | 1 | 2 | 0 | 0 | 1 | 4 |
| 59 | 2 | 3 | 0 | 0 | 2 | 4 |
| 60 | 3 | 1 | 2 | 0 | 0 | 3 |
| 61 |  |  |  |  |  |  |
| 62 |  |  |  |  |  |  |
| 63 |  |  |  |  |  |  |

We claim:

1. A compound of formula:

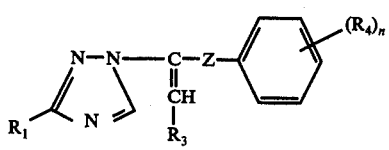

wherein $R_1$ is hydrogen, or nitro; $R_3$ is alkyl or $R_3$ is furyl, thienyl or phenyl optionally substituted with halogen, acyloxy, cyano, hydroxy, nitro, alkoxy or unsubstituted or halo-substituted alkyl; $R_4$ is hydrogen, halogen, nitro, phenyl, alkoxy or unsubstituted or halo-substituted alkyl; $n$ is 1, 2 or 3; and $Z$ is $C = O$, or a fungicidal salt of such a compound.

2. A compound as claimed in claim 1 wherein $R_3$ is propyl, phenyl, fluorophenyl, chlorophenyl, nitrophenyl, methoxyphenyl, butoxyphenyl, cyanophenyl, hydroxyphenyl, acetoxyphenyl, dichlorophenyl, dimethoxyphenyl, biphenyl, 2-thienyl or 2-furyl.

3. A compound as claimed in claim 2 wherein $R_4$ is hydrogen, fluorine, chlorine or phenyl.

4. A fungicidal composition comprising, as active ingredient, a fungicidally effective amount of a compound or salt as claimed in claim 1, and a carrier for the active ingredient.

5. A fungicidal composition comprising, as active ingredient, a fungicidally effective amount of a compound or salt as claimed in claim 2, and a carrier for the active ingredient.

6. A fungicidal composition comprising, as active ingredient, a fungicidally effective amount of a compound or salt as claimed in claim 3, and a carrier for the active ingredient.

7. A method of combating fungal diseases in a plant, the method consisting essentially of the step of applying to the plant, to seed of the plant or to the locus of the plant or seed, a fungicidally effective amount of a compound or salt as claimed in claim 1.

8. A method of combating fungal diseases in a plant, the method consisting essentially of the step of applying to the plant, to seed of the plant or to the locus of the plant or seed, a fungicidally effective amount of a compound or salt as claimed in claim 2.

9. A method combating fungal diseases in a plant, the method consisting essentially of the step of applying to the plant, to seed of the plant or to the locus of the plant or seed, a fungicidally effective amount of a compound or salt according to claim 3.

10. A compound as claimed in claim 3 wherein $R_1$ is hydrogen.

11. A compound as claimed in claim 3 wherein $n$ is 1.